(12) United States Patent
Lee et al.

(10) Patent No.: US 8,522,629 B2
(45) Date of Patent: Sep. 3, 2013

(54) SEQUENTIAL GROUNDWATER SAMPLER AND SAMPLING METHOD THEREOF

(75) Inventors: Bong Joo Lee, Daejeon (KR); Yong Je Kim, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 510 days.

(21) Appl. No.: 12/807,069

(22) Filed: Aug. 26, 2010

(65) Prior Publication Data
US 2011/0120238 A1 May 26, 2011

(30) Foreign Application Priority Data
Nov. 23, 2009 (KR) .......................... 10-2009-0113200

(51) Int. Cl.
*G01N 1/12* (2006.01)
(52) U.S. Cl.
USPC .............................. 73/864.35; 73/864; 73/863
(58) Field of Classification Search
USPC ...................... 73/863, 864, 864.35
See application file for complete search history.

(56) References Cited

U.S. PATENT DOCUMENTS

| | | | |
|---|---|---|---|
| 4,538,683 A | 9/1985 | Chulick | |
| 5,279,337 A * | 1/1994 | Ringot et al. | 141/1 |
| 5,293,931 A | 3/1994 | Nichols et al. | |
| 5,454,275 A * | 10/1995 | Kabis | 73/864.51 |
| 5,485,881 A | 1/1996 | Toon et al. | |
| 5,546,818 A * | 8/1996 | Keefer | 73/863 |

* cited by examiner

Primary Examiner — Hezron E Williams
Assistant Examiner — Rodney T Frank
(74) Attorney, Agent, or Firm — Rabin & Berdo, P.C.

(57) ABSTRACT

The present invention relates to a sequential groundwater sampler and a sampling method thereof, and more particularly, the sampler is constructed with a first pipe, a second pipe, a first cylinder unit and a second cylinder unit. The first pipe plays a role as a container for vacuum sample bottle. The first pipe is fixedly inserted to the second pipe. The second pipe is connected to the two cylinders to be moved up and down vertically while surrounding the first pipe by an advance and retreat of the second cylinder unit. The second pipe plays a role of, passing a syringe needle amounted at the end of a first piston in the first cylinder unit through a rubber plug of a vacuum sample bottle at the bottom end of the first pipe, or separating the syringe needle from the vacuum sample bottle, by an advance and retreat of the first cylinder unit. If the second cylinder and the first cylinder sequentially advance, groundwater is injected to the vacuum sample bottle at the bottom end of the first pipe. If the first cylinder unit and the second cylinder unit sequentially retreat, the vacuum sample bottle completed with injection of the sample is separated downward from the first pipe gravity. The present invention is related to the sampler and the method that sequentially sampling groundwater at a particular depth in a well through repeating above processes.

6 Claims, 8 Drawing Sheets

SEQUENTIAL GROUNDWATER SAMPLER AND SAMPLING METHOD THEREOF

CROSS-REFERENCE TO RELATED PATENT APPLICATION

This application claims the benefit of Korean Patent Application No. 10-2009-0113200, filed on Nov. 23, 2009, in the Korean Intellectual Property Office, the disclosure of which is incorporated herein in its entirety by reference.

BACKGROUND OF THE INVENTION

1. Field of the Invention

The present invention relates to a sequential groundwater sampler and sampling method thereof, capable of sequential sampling at specific depth in a well.

2. Description of the Related Art

For precise analysis for sequential change of groundwater quality in particular area of examination, a development of device capable of sequential sampling at a specific depth in a well is required.

Most of the sequential sampling devices for groundwater in a well employ pumps such as suction lift pumps, down-well centrifugal pumps and the like. However, when pumps are used for sampling groundwater, vertical flow of groundwater in the well is disturbed to make sampling a representative sample of groundwater at specific depth difficult, and there is a concern about possible aeration by contact with air as well as a loss of volatile organic component.

The applicant of the present invention already applied for "groundwater sampler using air cylinder and operating method thereof" (registration number: 10-0557481, registration date: 2006.02.24) to sample groundwater without a disturbance or a loss of volatile organic component in the groundwater. However, when groundwater is sampled sequentially, troublesome processes of repeatedly lifting up the sampler to withdraw the sampled groundwater and installing the sampler in the well are required. The present invention has improved the prior samplers to provide a sampler capable of sequential sampling groundwater without reinstallation.

SUMMARY OF THE INVENTION

To solve the above problems, it is therefore an object of the present invention to provide a sequential groundwater sampler and sampling method thereof, capable of sequential sampling after installing the sampler at a specific target depth in a well.

The objects and advantages of the present invention will be described below and will be known by embodiments of the present invention. The objects and advantages of the present invention will be embodied by the means and its combinations represented in the claims.

The present invention, a sequential groundwater sampler as means to solve above problems includes: a first pipe as a container for the vacuum sample bottles with a weight pendulum on the vacuum sample bottles top ends to move down the vacuum sample bottles inside of the pipe by gravity; a second pipe moving up and down in a vertical direction while surrounding the first pipe according to an advance and retreat of a second cylinder; a first cylinder unit to pass a syringe needle through the vacuum sample bottles for sampling groundwater at a target depth in a well; a second cylinder unit to move up and down the second pipe and the first cylinder unit or discharge vacuum sample bottles. The sequential groundwater sampler includes a guide protrusion protruded on outer circumferential surface of the first pipe to control a linear movement of the second pipe; a plate spring of arch form outwardly protruded to control a downward movement of the vacuum sampling bottles mounted on the first pipe; a supporting body fixedly interconnecting the second pipe, the first cylinder unit and the second cylinder unit so that the first pipe is fixed in a predetermined length inside the second pipe; an opening to discharge the vacuum sampling bottles completed with injection of groundwater; an opening in lengthwise direction on a sloped surface sloped downward to inject groundwater into the vacuum sample bottles through the injection unit; a discharge line being extended and sloped downward toward outside from the opening to discharge the vacuum sample bottles; and a pickup box receiving the vacuum sample bottles discharged and dropped outside from the sampler after injection of groundwater into vacuum sample bottles.

The injection unit comprises: a main syringe unit vertically moved up or down by the first cylinder unit; a fixing body protecting the syringe needle; and a protecting pipe body coupled to an outside of the main syringe unit to protect the main syringe unit and formed with an external inlet on an outer circumferential surface thereof to inflow groundwater inside.

The supporting body comprises: a plurality of first fixing plates fixedly coupled on an outer circumferential surface of the first pipe; a plurality of second fixing plates fixedly coupled on an outer circumferential surface of the second cylindrical unit; and a plurality of supporting bars interconnecting the first fixing plates and the second fixing plates to fix the inserted one end of the first pipe by the predetermined length into the second pipe.

The first pipe forms with a plate spring of arch form protruded outwardly at a mid part thereof so that the second pipe applies pressure outside of the plate spring not to move down the vacuum sample bottles inside the first pipe when the second pipe moves down, and so that the pressure applied on the plate spring disappears and the vacuum sample bottles inside the first pipe moves down by corresponding and fitting the plate spring to an opening hole on an outer circumferential surface of the second pipe when the second pipe moves up.

The sampling method of this sequential groundwater sampler comprises; step S100 of moving up a second pipe and a first cylinder unit by a second cylinder unit to contact a sloped surface inside the second pipe with a bottom end part of the first pipe; step S110 of filling inside of the first pipe with a plurality of vacuum sample bottles by directing a rubber plug part of the vacuum sample bottles to a bottom end of the first pipe; step S120 of inserting a weight pendulum into a top end of the plurality of vacuum sample bottles and coupling a cover to a top end part of the first pipe; step S130 of positioning the sampler at a target depth in a well; step S140 of moving up the syringe needle of the injection unit by the first cylinder unit to pass the syringe needle through the rubber plug of the vacuum sample bottles positioned at the inside bottom end of the first pipe; step S150 of inflowing groundwater into a syringe needle through external and internal inlets and storing groundwater in the vacuum sample bottles; step S160 of moving down the main syringe unit by the first cylinder unit to separate a syringe needle passing through the sample bottles from the sample bottles; step S170 of moving down the second pipe and the first cylinder unit by the second cylinder unit to space apart the sloped surface inside the second pipe from the bottom end part of the first pipe to externally discharge the vacuum sample bottle completed in injection with groundwater sample through an opening and a discharge line; step S180 of dropping the externally discharged vacuum sample bottle to a pickup box connected to the discharge line; and step 190 of moving down and positioning the vacuum sample bottle of next sequence at the position of the discharged vacuum sample bottle by a load of the weight pendulum.

BRIEF DESCRIPTION OF THE DRAWINGS

The above and other features and advantages of the present invention will become more apparent by describing in detail exemplary embodiments thereof with reference to the attached drawings in which.

BRIEF DESCRIPTION OF REFERENCE NUMBERS OF MAJOR ELEMENTS

Figure 1:
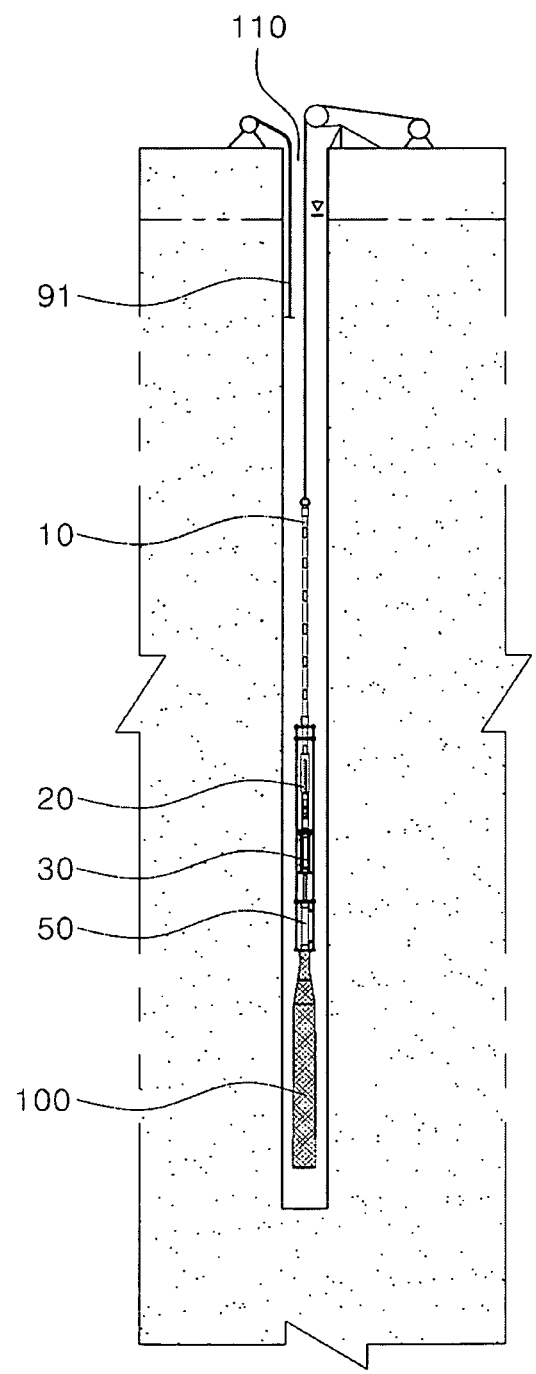
FIG. 1 is an exemplary view illustrating installed sampler in a well according to an embodiment of the present invention.

| 10: first pipe | 11: guide protrusion |
|---|---|
| 12: plate spring | 13: cover |
| 14: installation ring | 15: identification hole |
| 16: opening hole | 20: second pipe |
| 21: guide line | 22: opening |
| 23: sloped surface | 24: main opening |
| 25: discharge line | 26: connection hole |
| 27: opening hole | 30: first cylinder unit |
| 31: first piston | 40: injection unit |
| 41: main syringe unit | 42: main housing |
| 43: internal inlet | 44: syringe needle |
| 45: fixing body | 46: protecting pipe body |
| 47: external inlet | 50: second cylinder unit |
| 51: second piston | 60: supporting body |
| 61: first fixing plate | 62: second fixing plate |
| 63: supporting bar | 70: weight pendulum |
| 80: vacuum sample bottle | 81: rubber plug |
| 90: fixing wire | 100: pickup box |
| 101: guide pipe | 102: flowing hole |

DETAILED DESCRIPTION OF THE INVENTION

The present invention has following characteristics to accomplish the object described above.

According to one exemplary embodiment of the present invention, a sequential groundwater sampler, installed at a target depth in a well, comprises: a first pipe installed in lengthwise direction at a predetermined length inside of the second pipe from an upper end of the second pipe, formed with a guide protrusion on an outer circumferential surface thereof and filled with a plurality of vacuum sample bottles inside thereof; a second pipe moving up and down in a vertical direction while surrounding the first pipe according to an advance and retreat of a second cylinder; a first cylinder unit installed at a bottom end of the second pipe; an injection unit moves up or down by the first cylinder unit and positioned inside the second pipe; a second cylinder unit installed at a bottom end of the first cylinder unit and moves up or down the first cylinder unit and the first pipe; a supporting body fixedly interconnecting the first pipe and the second cylinder unit to install the first pipe at the predetermined length inside the second pipe; and a pendulum weight at a top end in the first pipe to move the vacuum sample bottles by gravity, wherein the vacuum sample bottles fill the first pipe for a rubber plug of the vacuum sample bottles to be directed bottom end of the first pipe.

The second pipe comprises: a guide line correspondingly fitted with the guide protrusion to guide the second pipe in a vertical direction when the second pipe is moved up or down; an opening to externally discharge the vacuum sample bottle; a main opening inside the opening in lengthwise direction formed on a sloped surface sloped to collect groundwater at the vacuum sample bottle through the injection unit; a discharge line formed extended and sloped downward outside from the opening to externally discharge the vacuum sample bottle; and a pickup box connected to a bottom end of the discharge line that receives the dropping vacuum sample bottle filled with groundwater.

The injection unit comprises: a main syringe unit vertically moved up or down by the first cylinder unit, formed with a syringe needle at one end thereof and formed with a perforated internal inlet to inflow groundwater into the syringe needle; a fixing body protecting the syringe needle formed on an outside circumferential surface of the syringe needle; and a protecting pipe body coupled to an outside of the main syringe unit to protect the main syringe unit and formed with an external inlet on an outer circumferential surface thereof to inflow sample inside.

The supporting body comprises: a plurality of first fixing plates fixedly coupled on an outer circumferential surface of the first pipe; a plurality of second fixing plates fixedly coupled on an outer circumferential surface of the second cylindrical unit; and a plurality of supporting bars interconnecting the first fixing plates and the second fixing plates to fix the inserted one end of the first pipe by the predetermined length into the second pipe.

The first pipe forms with a plate spring of arch form protruded outwardly at a mid part thereof so that the second pipe applies pressure outside of the plate spring not to move down the vacuum sample bottles inside the first pipe when the second pipe moves down, and so that the pressure applied on the plate spring disappears and the vacuum sample bottles inside the first pipe moves down by corresponding and fitting the plate spring to an opening hole on an outer circumferential surface of the second pipe when the second pipe moves up.

A sampling method of a sequential groundwater sampler as one exemplary embodiment comprises; step S100 of moving up a second pipe and a first cylinder unit by a second cylinder unit to contact a sloped surface inside the second pipe with a bottom end part of the first pipe; step S110 of filling inside of the first pipe with a plurality of vacuum sample bottles by directing a rubber plug part of the vacuum sample bottle to a bottom end of the first pipe; step S120 of inserting a weight pendulum into a top end of the plurality of vacuum sample bottles and coupling a cover to a top end part of the first pipe; step S130 of positioning the sampler at a target depth in a well; step S140 of moving up a main syringe unit of an injection unit by the first cylinder unit to pass the main syringe unit through the rubber plug of the vacuum sample bottle positioned at the inside bottom end of the first pipe; step S150 of inflowing groundwater into a syringe needle through external and internal inlets and storing groundwater in the vacuum sample bottle; step S160 of moving down the main syringe unit by the first cylinder unit to separate a syringe needle passing through the sample bottle from the sampling bottles; step S170 of moving down the second pipe and the first cylinder unit by the second cylinder unit to space apart the sloped surface inside the second pipe from the bottom end part of the first pipe to externally discharge the vacuum sample bottle completed in injection with groundwater through an opening and a discharge line; step S180 of dropping the externally discharged vacuum sample bottle to a pickup box connected to the discharge line; and step 190 of moving down and positioning the vacuum sampling bottle of next sequence at the position of the discharged vacuum sample bottle by a load of the weight pendulum.

Before describing the various embodiments according to the present invention, it will be understood that the application shall not be limited by the details of the configuration and arrangement of the elements set forth in the following detail description of drawings. The present invention may be realized in various other embodiments and may be performed in diverse methods. It will be understood that the terms such as directions of devices or elements (for example "front", "back", "up", "down", "top", "bottom", "left", "right", "lateral" and so on) and the like are used to simplify the explanation of the present invention and shall not be interpreted as having meaning that related devices or elements should have such particular directions. Further, the terms like "first" and "second" used in the specification and claims for explanation are not intended to represent or mean a relative importance or any other purpose.

The present invention will now be described more fully hereinafter with reference to the accompanying drawings, in which preferred embodiments of the invention are shown. It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

Accordingly, since the embodiments set forth in the present specification and the configurations illustrated in the drawings are shown by way of example and do not represent all the technological spirit of the present invention, it should be understood that embodiments of the present invention are capable of various modifications, equivalents, and alternatives at the time of present application.

Figure 2:
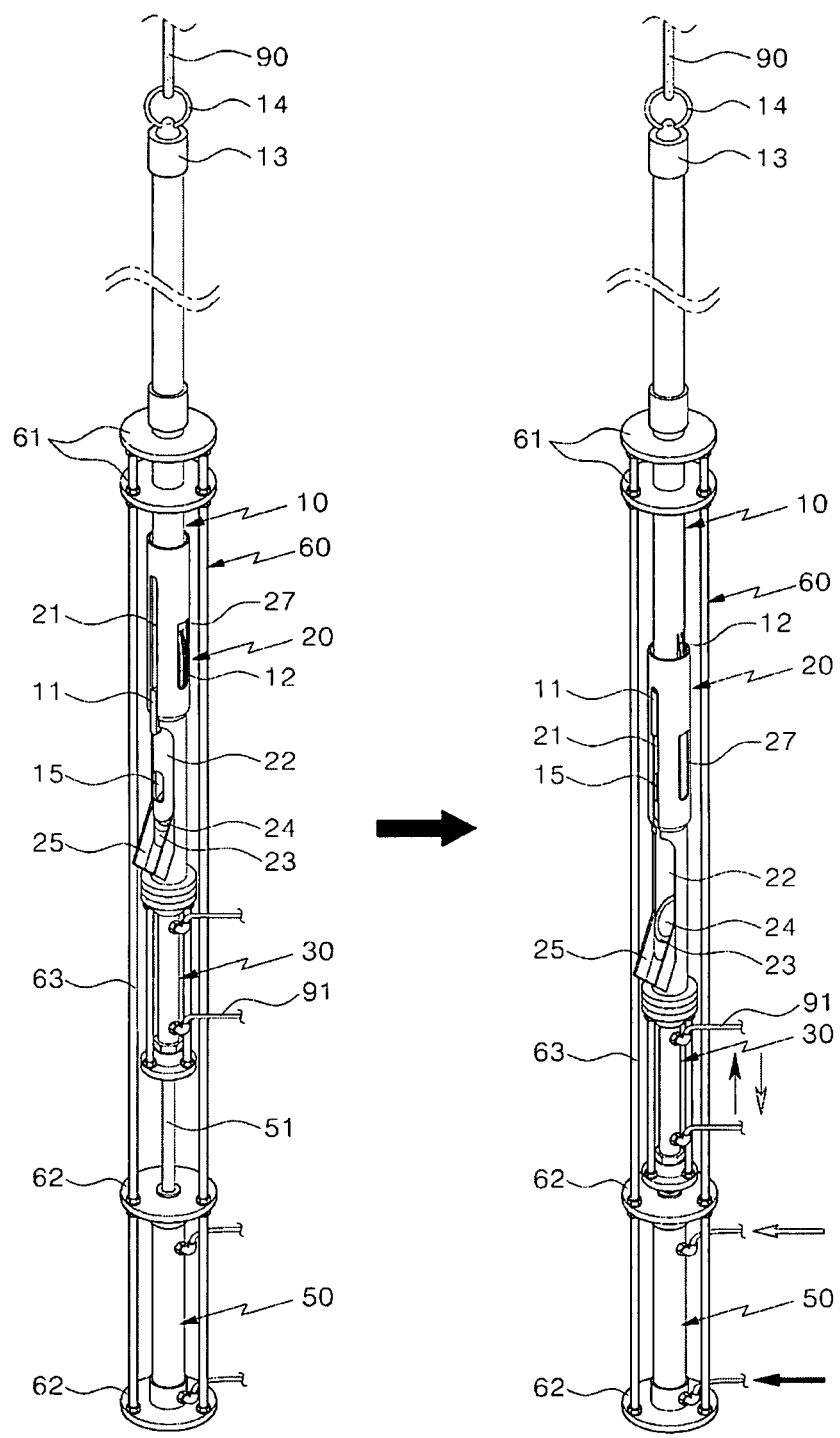
FIG. 2 is a perspective view illustrating a first cylinder unit and a second pipe being moved up and down by a second cylinder unit according to an exemplary embodiment of the present invention.
Figure 3:
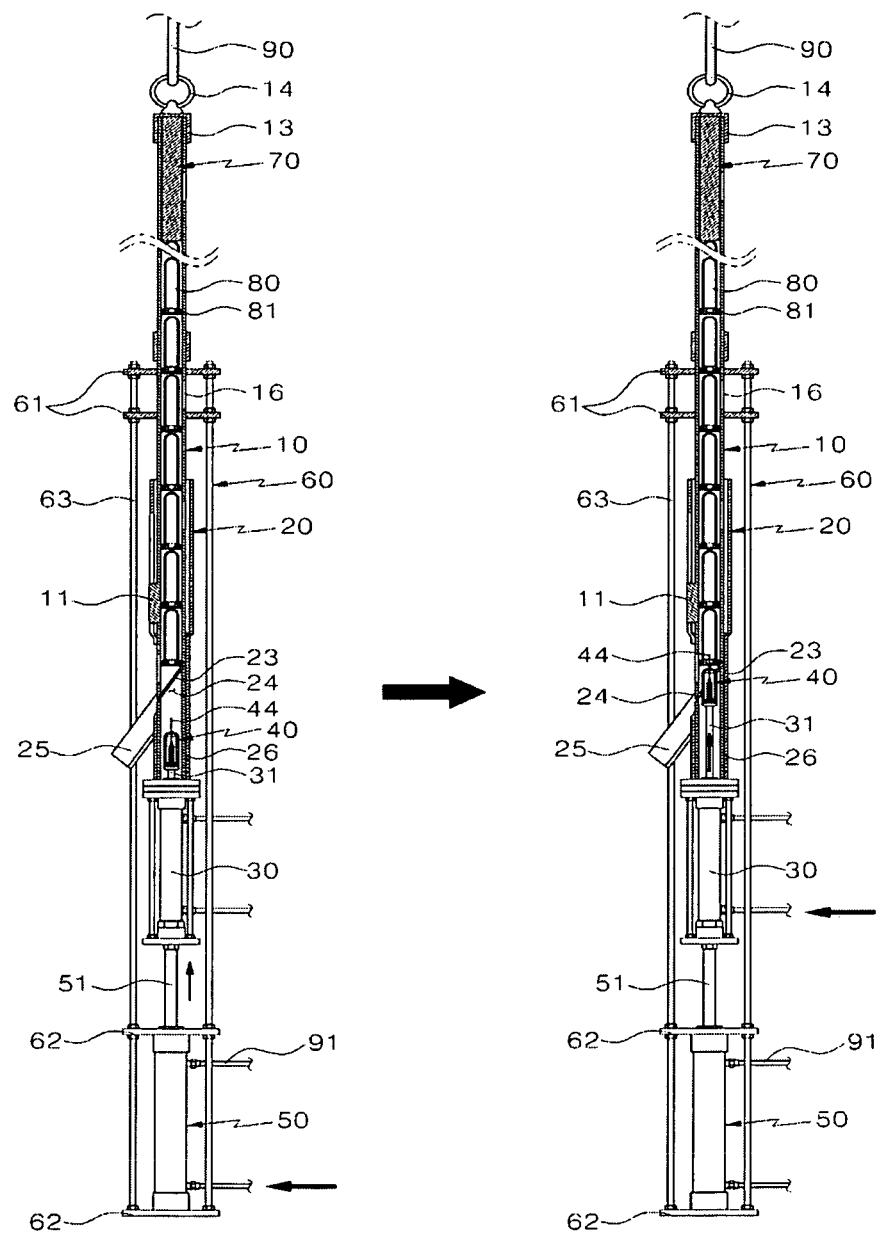
FIG. 3 is a cross sectional view illustrating an injection unit being moved up by the first cylinder unit according to an exemplary embodiment of the present invention.
Figure 4:
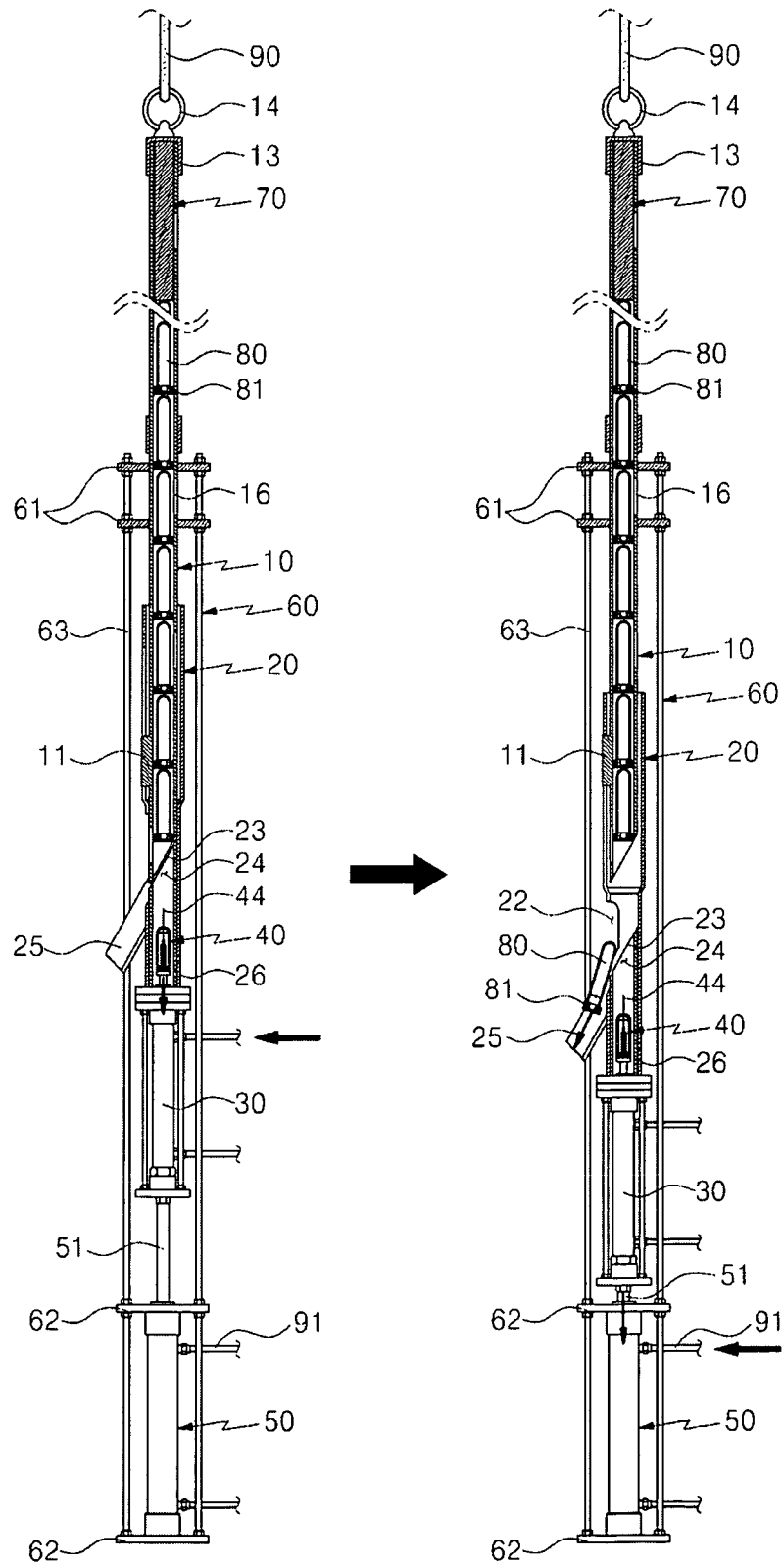
FIG. 4 is a view illustrating the first cylinder unit and the second pipe being moved up by the second cylinder unit, after collecting sample in the sample bottle and moving down the injection unit by the first cylinder unit according to an exemplary embodiment of the present invention.
Figure 5:
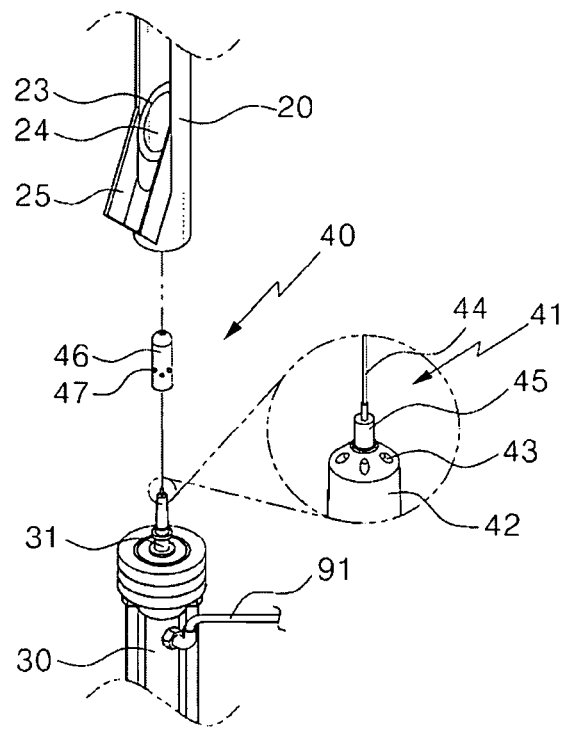
FIG. 5 is an exploded perspective view illustrating the injection unit according to an exemplary embodiment of the present invention.
Figure 6:
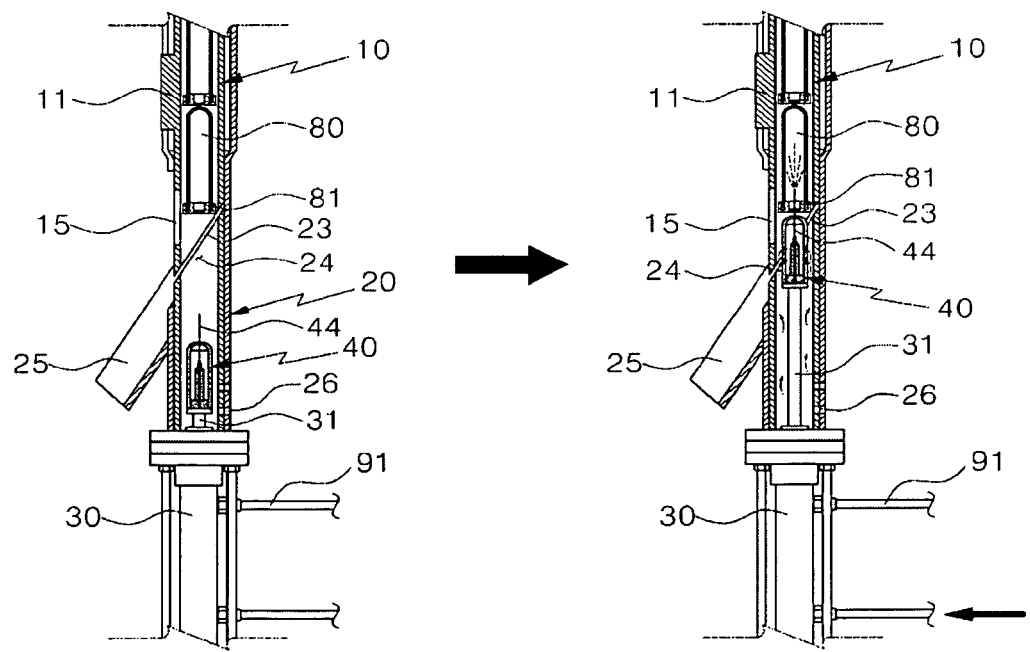
FIG. 6 is a cross sectional view illustrating a sampling operation of the injection unit according to an exemplary embodiment of the present invention.
Figure 7:
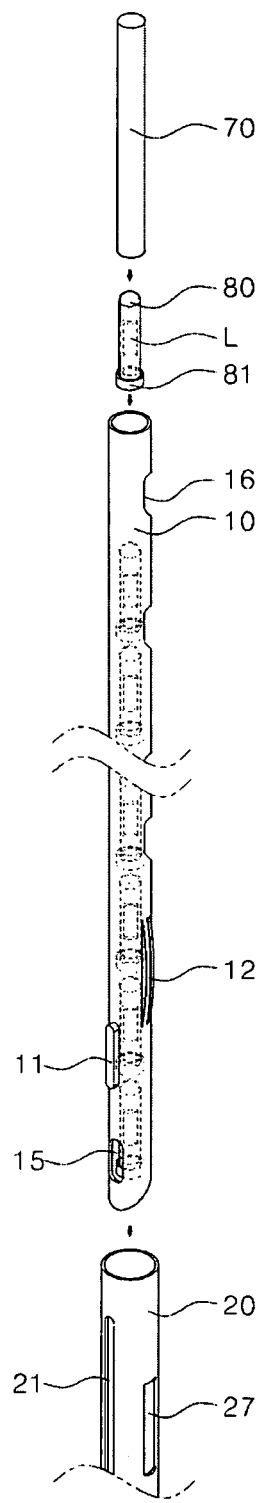
FIG. 7 is a perspective view illustrating the first pipe according to an exemplary embodiment of the present invention.
Figure 8:
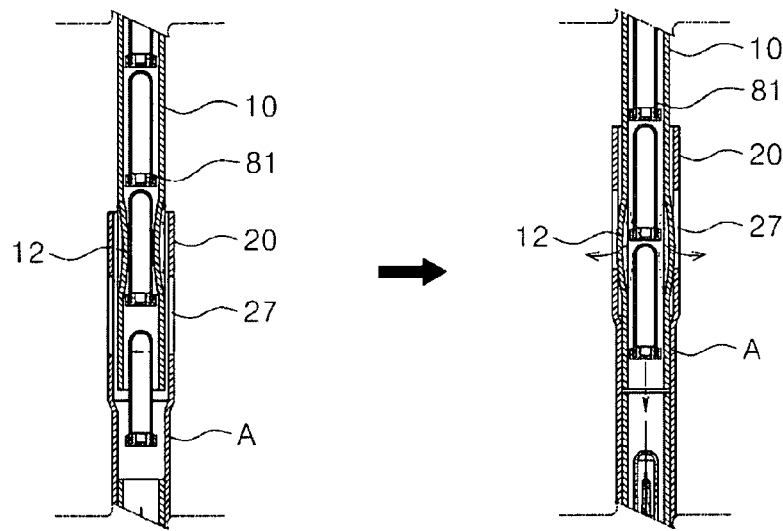
FIG. 8 is a cross sectional view illustrating a plate spring according to an exemplary embodiment of the present invention.
Figure 9:
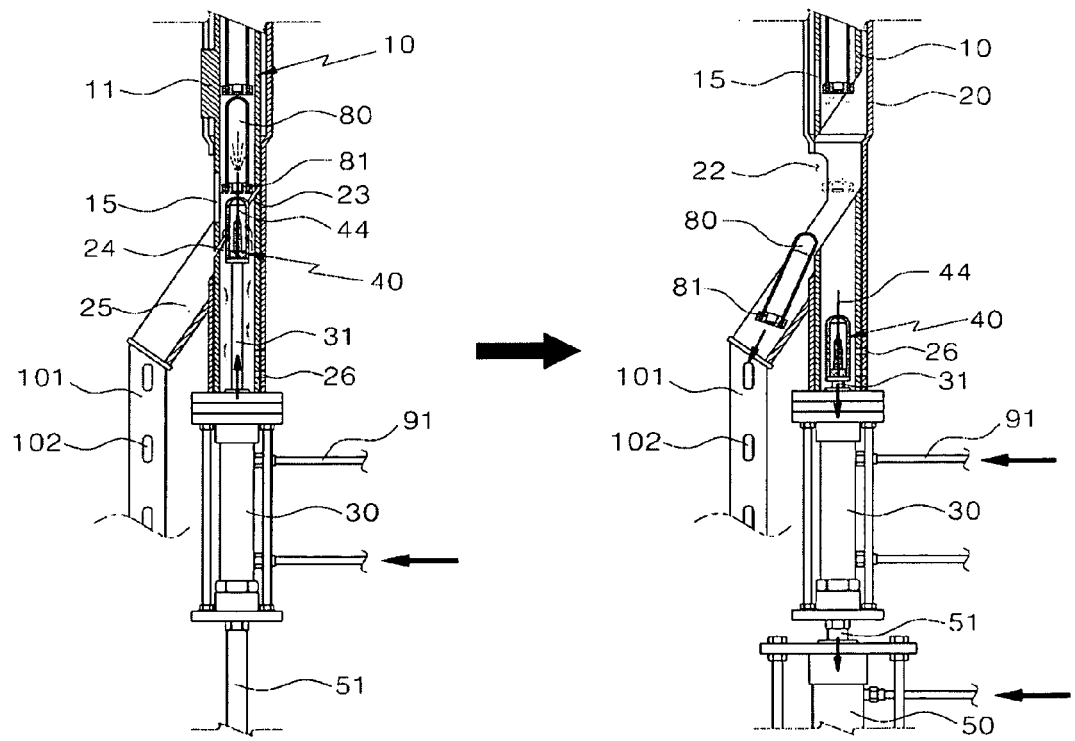
FIG. 9 is a cross sectional view illustrating the vacuum sample bottle being discharged according to an exemplary embodiment of the present invention.
Figure 10:
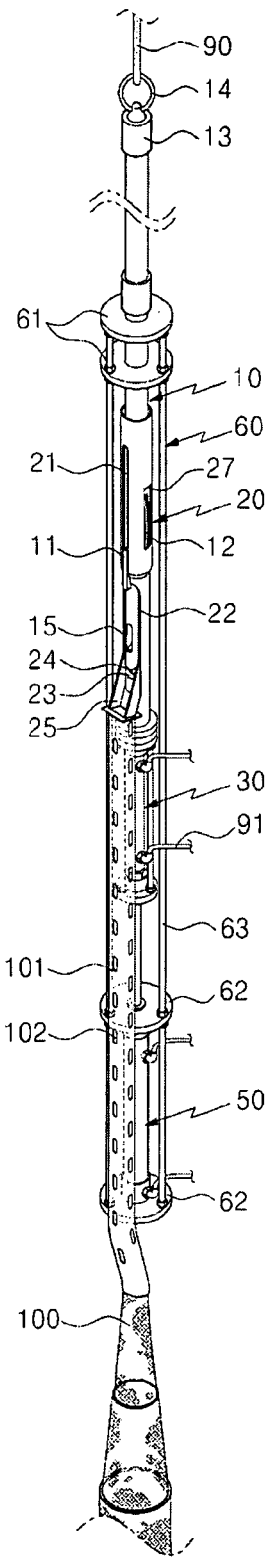
FIG. 10 is a perspective view illustrating the pickup box connected to the discharge line according to an exemplary embodiment of the present invention.

Hereinafter, a sequential groundwater sampler and sampling method thereof according to a preferable embodiment of the present invention will be described in detail referring to FIGS. 1 through 10.

As illustrated, the sequential groundwater sampler and sampling method thereof includes a first pipe 10, a second pipe 20, a first cylindrical unit 30, an injection unit 40, a second cylinder unit 50, a supporting body 60, and a weight pendulum 70.

The first pipe 10 identical to the second pipe 20 as described later is open at its opposite ends and have circular cross section of hollow pipe shape in lengthwise direction but has a diameter relatively smaller than the second pipe 20 to insert a predetermined length of its top end into the second pipe 20. (After inserting the predetermined length of the first pipe to the top end of the second pipe 20, fixing of the inserted location is solved by the supporting body 60 described later.)

A plurality of vacuum sample bottles 80 coupled in a cap type with a rubber plug 81 of rubber material at their one ends have circular cross sections and fill an interior of the first pipe 10. At this time, the plurality of the vacuum sample bottles 80 fill the first pipe 10 in lengthwise direction by aligning the ends of the vacuum sample bottles 80 coupled with the rubber plug 81 to be directed below. The pendulum weight 70 of a predetermined weight is inserted at a top end of the vacuum sample bottle 80 filling for the last time, that is, a top inside end of the first pipe 10. The inserted pendulum weight 70 works for the vacuum sample bottles 80 to move to a downward direction in the first pipe 10 by gravity when the sampler is sequentially operated and not to be pushed upward when the syringe needle passes the vacuum sample bottle 80 through the rubber plug 81 by moving up the first cylinder unit 30 and the second cylinder unit 50.

A guide protrusion 11 having a predetermined length is formed protruded on an outer circumferential surface of the first pipe 10 in lengthwise direction of the first pipe 10. A predetermined length of the first pipe 10 is inserted into the second pipe 20 to fit the guide protrusion 11 to a guide line 21 so that the guide protrusion 11 moves up and down along the guide line 21 to guide a vertical up and down movement of the second pipe 20 when the second pipe 20 moves up and down by the second cylinder unit 50 described later.

A plate spring 12 is formed on an outer circumferential surface of the first pipe 10 to be positioned relatively higher than the guide protrusion 11 formed protruded. The plate spring 12 forms an arch shape on the outer circumferential surface of the first pipe 10 to be protruded outside of the first pipe 10. This causes an inner circumferential surface of the second pipe 20 to apply pressure to the plate spring 12 formed protruded at the outer circumferential surface of the first pipe 10 when the second pipe 20 inserted with the first pipe 10 moves up and down. Then, the pressed plate spring 12 applies pressure to the vacuum sample bottles 80 filling the interior of the first pipe 10 lengthwise so that the vacuum sample bottles 80 do not move down. That is, referring FIG. 2 and as illustrated in right side of FIG. 2, if the second pipe 20 while being inserted with the first pipe 10 moves down, the plate spring 12 formed protruded at the first pipe 10 is applied of pressure by the inner circumferential surface of the second pipe 20 so that the vacuum sample bottles 80 do not move down. As illustrated in left side of FIG. 2, if the second pipe 20 moves up while being inserted with the first pipe 10 and correspondingly fitted with an opening hole 27 on the second pipe 20, the applied pressure disappears through restoring to an original state by the plate spring 12 being fitted to the opening hole 27 so that the vacuum sample bottles 80 filling the interior of the first pipe 10 move down. In other words, the pressure applied to the plate spring 12 disappears and restores to the original state when the plate spring 12 is fitted to the opening hole 27, that is, when the second pipe 20 moves up to collect groundwater in the vacuum sample bottle 80 and the bottom end of the first pipe 10 contacts the sloped surface 23 of the second pipe 20. (Arch shape of the plate spring 12 is formed protruded outside of the first pipe 10 mid part. The plate spring is responsible for fixing the vacuum sample bottles 80 positions, through being pressed by the inner circumferential surface of the second pipe 20 top end so that the vacuum sample bottles do not move down any more but fixed at their positions when the second pipe 20 moves down, and through relieving the pressure applied to the plate spring 12 by the opening hole 27 so that the vacuum sample bottles 80 in the first pipe 10 move down when the second pipe 20 moves up.)

After inserting the plurality of the vacuum sample bottles 80 and the weight pendulum 70 into the first pipe 10, a cover 13 formed with an installation ring 14 is coupled to the top end of the first pipe 10. A fixing wire 90 connected on the ground is connected to the installation ring 14 so that the sampler of the present invention is installed in a well 110.

A plurality of opening holes 16 are formed perforated in equal distance toward lengthwise direction on the outer circumferential surface of the first pipe 10 to confirm the position of the vacuum sample bottles 80 filling the interior of the first pipe 10 as well as to smoothly move the vacuum sample bottles 80 downward by freely flowing the groundwater in the first pipe 10.

The second pipe 20 is open at its opposite ends and have circular cross section of hollow pipe shape in lengthwise direction. (Obviously, according to a users choice, the second pipe 20 may have various shapes. Since the second pipe 20 has circular pipe shape cross section, the other constituting elements connected to the second pipe 20 will obviously have identical shape.)

A guide line 21 opened on the outer circumferential surface of the second pipe 20 is formed in the lengthwise direction. The guide protrusion 11 of the first pipe 10 described later is correspondingly fitted with the guide line 21. An opening 22 at one end of the guide line 21 of the second pipe 20 is in lengthwise direction. The sloped surface 23 sloped downward in lengthwise direction is formed inside of the opening 22 (interior of the second pipe 20). The sloped surface 23 is sloped downward toward the opening 22. In the opening 22, a main opening 24 is formed, and a discharge line 25 is formed extended and sloped downward outside from the opening 22. The discharge line 25 and the sloped surface are sloped downwardly at same sloped angle.

Further, the second pipe 20 has a circular cross section. A part of the second pipe 20 where the opening 22 is formed has a narrower diameter than the part of the second pipe 20 where the guideline 21 is formed ('A' part in FIG. 8).

A pickup box 100 is connected to an end of the discharge line 25 to receive the vacuum sample bottles 80 discharged and gravity dropped through the opening 22.

(Since the pickup box 100 is also installed in the well, the pickup box 100 takes a net shape installed with a separate weight pendulum on a bottom surface thereof. According to various exemplary embodiments of users, various forms of smoothly dropping the vacuum sample bottles 80 from the discharge line 25 to the pickup box 100 may be variously modified including interconnecting the pickup box 100 with the discharge line 25 and providing a guide pipe 101 with multiple flowing holes 102 perforated on an outer circumferential surface thereof, and the like to flow the groundwater, only if the pickup box 100 has a shape safely and correctly receiving the vacuum sample bottles 80 injected with the groundwater and dropped by gravity.)

The first cylinder unit 30 is installed upright at a bottom end of the second pipe 20 and the injection unit 40 moved up by the first cylinder unit 30 is coupled to a top end of the first cylinder unit 30. That is, the cylinder unit 30 is installed at the bottom end of the second pipe 20 to position the injection unit 40 coupled to the top end of the first cylinder unit 30 inside of the one end of the second pipe 20.

The injection unit 40 is moved up by the first cylinder unit 30. The injection unit includes, a main housing 42, a main syringe unit 41, a fixing body 45 and a protecting pipe body 46. A plurality of internal inlets 43 is formed perforated on a top outer circumferential surface of the main housing 42 to inflow external groundwater inside thereof. The main syringe unit 41 is formed of a syringe needle 44 operatively connected to the main housing 42 in vertical direction at top end of the main housing 42. The fixing body 45 is coupled to a connection portion between the main housing 42 and the syringe needle 44 on an outer circumferential surface of the syringe needle 44 to protect the syringe needle 44. The protecting pipe body 46 is coupled to an outer circumferential surface of the main syringe unit 41 to protect the fixing body 45 and the main syringe unit 41. A plurality of external inlets 47 is formed on an outer circumferential surface of the protecting pipe body 46.

(Obviously, a first piston 31 of the first cylinder unit 30 is fixedly connected with one end of the main housing 42 to move up the injection unit 40 by the first cylinder unit 30.)

If the injection unit 40 is moved up by the first cylinder unit 30, the syringe needle 44 passes the rubber plug 81 of the vacuum sample bottle 80 in the first pipe 10 through the main opening 24 of the sloped surface 23. At the same time, the groundwater moves to the syringe needle 44 through the external inlet 47 of the protecting pipe body 46 and the internal inlet of the main syringe unit 41. Then, the groundwater is sprayed inside the vacuum sample bottle through the syringe needle 44.

The second cylinder unit 50 is fixedly installed upright at a bottom end of the first cylinder unit 30. A second piston 51 of the second cylinder unit 50 is fixedly connected with a bottom end of the first cylinder unit 30 to move up and down the first cylinder unit 30 by the second cylinder unit 50. Since the second pipe 20 is fixedly installed upright at a top end of the first cylinder unit 30, the first cylinder unit 30 moves together with the second pipe 20.

(Each of the first cylinder unit 30 and the second cylinder unit 50 are identically connected with multiple of hoses 91 at their top and bottom ends. Obviously, air is selectively injected through the hoses 91 (Pneumatic pressure was used in the present invention.) to move up and down the first piston 31 and second pistons 51 of the first cylinder unit 30 and the second cylinder unit 50. Obviously, the one ends of the multiple of hoses 91 which one ends are connected with the first cylinder unit 30 and the second cylinder unit 50 should be supplied with pneumatic pressure from the ground. For this, a pneumatic pump must be provided on the ground)

The supporting body 60 is to fix the position of the first pipe 10 inserted inside of the second pipe 20 by the predetermined length from the second pipe 20 top end. The supporting body 60 includes a plurality of first fixing plates 61, a second fixing plate 62, and a plurality of supporting bars 63. The plurality of first fixing plates 61 is formed protruded from an outer circumferential surface of the first pipe 10. The second fixing plate 62 is formed protruded from an outer circumferential surface of the second cylinder unit 50. The plurality of supporting bars 63 connects between the multiple of the first fixing plates 61 and the second fixing plate 62.

Hereinafter, the operation and principle of a preferred exemplary embodiment of the present invention having the above configuration and structure are described.

Obviously, a preliminary work of drilling the well 110 for sampling the groundwater at particular region should be completed for a user to collect the groundwater sample by the sampler according to the present invention.

1. Step S100: The second pipe 20 and the first cylinder unit 30 are moved up by the second cylinder unit 50 so that the slope surface 23 inside the second pipe 20 contacts the bottom end of the first pipe 10. That is, through contacting the sloped surface 23 inside the second pipe 20 to the bottom end of the first pipe 10 by moving the second pipe 20 upward, the plurality of vacuum sample bottles 80 filling the first pipe 10 do not escape through the bottom end side of the first pipe 10.

2. Step S110: After step S100, for the syringe needle 44 in the injection unit 40 to pass through the rubber plug 81 part of the vacuum sample bottle 80 filling the interior of the first pipe 10, the first pipe 10 is filled with the plurality of vacuum sample bottles 80 by directing the rubber plug 81 part in the first pipe 10 downward.

3. Step S120: After step S110, the weight pendulum 70 is inserted at the top of the plurality of vacuum sample bottles 80 and the cover 13 is coupled to the top end part of the first pipe 10 in this step. When the sampler filled with the vacuum sample bottles 80 of the present invention is installed in the well 110, the vacuum sample bottles 80 which interiors are vacant are floated upward. The load of the weight pendulum 70 presses the vacuum sample bottles to be moved downward by gravity. At this time, since the plate spring 12 formed protruded on the outer circumferential surface of the first pipe 10 is fitted to the opening hole 27 of the second pipe 20, the plate spring dose not press for the position of the vacuum sample bottles 80 to be fixed.

4. Step S130: After step S120, the fixing wire 90 is connected to the installation ring 14 of the cover 13 coupled at the top end of the first pipe 10. The sampler of the present invention is positioned at the target depth in the groundwater well 110 by loosening the fixing wire 90 from the ground. Obviously, before moving down the sampler, the plurality of hoses 91 should be connected respectively to move the first cylinder unit 30 and the second cylinder unit 50

5. Step S140: After step S130, if the sampler of the present invention positioned at the certain depth, air is injected to the first cylinder unit 30 to move up the first piston 31 of the first cylinder unit 30 that moves up the main syringe unit 41 of the injection unit 40. The main syringe unit 41 is moved up and passes through the rubber plug 81 of the vacuum sample bottle 80 positioned at the bottom end of the first pipe 10. When the main syringe unit 41 passes through the rubber plug 81 and the vacuum sample bottle 80, the weight pendulum 70 applies its load to the plurality of the vacuum sample bottles 80 and the vacuum sample bottles 80 are not moved up but fixed.

6. Step S150: When the main syringe unit 41 passes through the vacuum sample bottles through step S140, the groundwater flows inside the protecting pipe body 46 through the external inlet 47 of the protecting pipe body 46. The groundwater flowed in the protecting pipe body 46 is moved to the syringe needle 44 through the internal inlet 43 of the main syringe unit 41, sprayed to and stored in the vacuum sample bottle 80.

7. Step S160: After step S150, the main syringe unit 41 is moved down through the first cylinder unit 30 so that the syringe needle 44 of the main syringe unit 41 is separated from the rubber plug 81 of the vacuum sample bottle 80.

8. Step S170: After step S160, air is injected to the second cylinder unit 50, and the second pipe 20 and the first cylinder unit 30 are moved down. This causes the sloped surface 23 in the second pipe separated with the bottom end part of the first pipe 10. At the same time, the plate spring 12 fitted to the opening hole 27 of the second pipe 20 gets out from the opening hole 27 and the inner circumferential surface of the second pipe 20 presses the plate spring 12 so that the vacuum sample bottle 80 in the first pipe 10 is fixed at its position without moving down any more. The vacuum sample bottle 80 completed with an injection of the groundwater positioned at the bottom end of the first pipe 10 gains a certain weight and moves down by gravity through the opening 22 and the discharge line 25.

9. Step 180: After step 170, the vacuum sample bottle 80 discharged out of the sampler through the discharge line 25 drops into the well 110. The vacuum sample bottle 80 guided by the discharge line 25 is dropped and collected into the pickup box 100.

10. Step 190: After step S180, if the second pipe 20 is moved up by operating the second cylinder unit 50, the plate spring 12 of the first cylinder 10 is fitted to the opening hole 27. Then, the pressure applied to the plate spring is relieved and the plurality of empty vacuum sample bottles 80 inside the first pipe are moved down by the load of weight pendulum 70 positioned at the top end in the first pipe 10. This leads to position the other vacuum sample bottle 80 at the position where the vacuum sample bottle 80 discharged from the first pipe 10 has positioned.

(Obviously, after step 190, air is injected to the first cylinder unit 30 to move up the first piston 31 of the first cylinder unit 30 that moves up the main syringe unit 41 of the injection unit 40 as step 140. Then, the groundwater is injected inside the vacuum sample bottle 80 positioned at the position where the discharged vacuum sample bottle 80 has positioned to enable a sequential sampling.)

Reference number '26' not described above is a connection hole. It is a hole through which the groundwater can flow into the second pipe 20 so that the main syringe unit 41 is smoothly moved up at the bottom end of the sloped surface in the second pipe 20. The vacuum sample bottles 80 can be attached with labels numbered in order inserted into the first pipe 10. Reference number '15' is an identification hole. It is a hole to identify whether the vacuum sample bottle 80 to store groundwater sample sprayed from the injection unit 40 has positioned at the bottom end of the first pipe 10.

As described above, if a sequential groundwater sampling at different or same sampling depth is necessary in a well, the groundwater at different depths or at same depth can be sampled without repeating an installation of the sampler.

While the present invention has been particularly shown and described with reference to limited exemplary embodiments and drawings, it will be understood by those of ordinary skill in the art that various changes in form and details may be made therein without departing from the spirit and scope of the present invention as defined by the following claims.

What is claimed is:

1. A sequential groundwater sampler, installed at a target depth to sample groundwater in a well, comprising:
a second pipe installed vertically;
a first pipe installed in lengthwise direction at a predetermined length inside of the second pipe from an upper end of the second pipe, formed with a guide protrusion on an outer circumferential surface thereof and filled with a plurality of vacuum sample bottles inside thereof;
a first cylinder unit installed at a bottom end of the second pipe;
an injection unit moving up or down by the first cylinder unit and positioned inside the second pipe;

a second cylinder unit installed at a bottom end of the first cylinder unit and moving up or down the first cylinder unit and the first pipe;

a supporting body fixedly interconnecting the first pipe and the second cylinder unit to install the first pipe at the predetermined length inside the second pipe; and a weight pendulum at a top end in the first pipe to move the vacuum sample bottles by gravity, wherein the vacuum sample bottles fill the first pipe for a rubber plug of the vacuum sample bottles to be directed bottom end of the first pipe.

2. The sampler according to claim 1, wherein the second pipe comprises:

a guide line correspondingly fitted with the guide protrusion to guide the second pipe in a vertical direction when the second pipe is moved up or down;

an opening to externally discharge the vacuum sample bottle;

a main opening formed in lengthwise direction on a sloped surface sloped inside the opening to collect groundwater at the vacuum sample bottle through the injection unit;

a discharge line formed extended and sloped downward outside from the opening to externally discharge the vacuum sample bottle; and a pickup box connected to a bottom end of the discharge line that receives the dropping vacuum sample bottle stored with groundwater.

3. The sampler according to claim 1, wherein the injection unit comprises:

a main syringe unit vertically moved up or down by the first cylinder unit, formed with a syringe needle at one end thereof and formed with a perforated internal inlet to inflow groundwater into the syringe needle;

a fixing body protecting the syringe needle formed on an outside circumferential surface of the syringe needle; and a protecting pipe body coupled to an outside of the main syringe unit to protect the main syringe unit and formed with an external inlet on an outer circumferential surface thereof to inflow groundwater inside.

4. The sampler according to claim 1, wherein the supporting body comprises:

a plurality of first fixing plates fixedly coupled on an outer circumferential surface of the first pipe;

a plurality of second fixing plates fixedly coupled on an outer circumferential surface of the second cylindrical unit; and a plurality of supporting bars interconnecting the first fixing plates and the second fixing plates to fix the inserted one end of the first pipe by the predetermined length into the second pipe.

5. The sampler according to claim 1, wherein the first pipe forms with a plate spring of arch form protruded outwardly at a mid part thereof so that the second pipe applies pressure outside of the plate spring not to move down the vacuum sample bottles inside the first pipe when the second pipe moves down, and so that the pressure applied on the plate spring disappears and the vacuum sample bottles inside the first pipe moves down by corresponding and fitting the plate spring to an opening hole on an outer circumferential surface of the second pipe when the second pipe moves up.

6. A sampling method of a sequential groundwater sampler comprising;

moving up a second pipe and a first cylinder unit by a second cylinder unit so that a sloped surface inside the second pipe contacts with a bottom end part of a first pipe;

filling an inside of the first pipe with a plurality of vacuum sample bottles by directing a rubber plug part of the vacuum sample bottle to a bottom end of the first pipe;

inserting a weight pendulum into a top end of the plurality of vacuum sample bottles and coupling a cover to a top end part of the first pipe;

positioning the sampler at a target depth in a well;

moving up a main syringe unit of an injection unit by the first cylinder unit to pass the main syringe unit through the rubber plug of the vacuum sample bottle positioned at the inside bottom end of the first pipe;

inflowing groundwater into a syringe needle through external and internal inlets and storing the groundwater in the vacuum sample bottle;

moving down the main syringe unit by the first cylinder unit to separate a syringe needle passing through the sample bottle from the sampling bottles;

moving down the second pipe and the first cylinder unit by the second cylinder unit to space apart the sloped surface inside the second pipe from the bottom end part of the first pipe to externally discharge the vacuum sample bottle completed in injection with groundwater sample through an opening and a discharge line;

dropping the externally discharged vacuum sample bottle to a pickup box connected to the discharge line; and moving down and positioning the vacuum sampling bottle of next sequence at the position of the discharged vacuum sample bottle by a load of the weight pendulum.

* * * * *